(12) United States Patent
khowdiary et al.

(10) Patent No.: US 10,709,734 B2
(45) Date of Patent: Jul. 14, 2020

(54) METHOD OF MAKING METAL BASED CATIONIC SURFACTANT NANO PARTICLES AND THEIR USE

(71) Applicants: Manal Mohamed khowdiary, Makkah (SA); Nashwa Mostafa Saleh, Makkah (SA)

(72) Inventors: Manal Mohamed khowdiary, Makkah (SA); Nashwa Mostafa Saleh, Makkah (SA)

(73) Assignee: Umm-Al-Qura University, Makkah (SA)

( * ) Notice: Subject to any disclaimer, the term of this patent is extended or adjusted under 35 U.S.C. 154(b) by 0 days.

(21) Appl. No.: 14/389,314

(22) PCT Filed: Apr. 1, 2014

(86) PCT No.: PCT/IB2014/001752
§ 371 (c)(1),
(2) Date: Sep. 29, 2014

(87) PCT Pub. No.: WO2015/150857
PCT Pub. Date: Oct. 8, 2015

(65) Prior Publication Data
US 2017/0007642 A1    Jan. 12, 2017

(51) Int. Cl.
| | | |
|---|---|---|
| *A61K 33/24* | (2019.01) | |
| *A61K 9/14* | (2006.01) | |
| *A01N 59/02* | (2006.01) | |
| *A01N 25/10* | (2006.01) | |
| *A01N 59/16* | (2006.01) | |
| *C01B 19/00* | (2006.01) | |
| *A61P 35/00* | (2006.01) | |

(52) U.S. Cl.
CPC ............. *A61K 33/24* (2013.01); *A01N 25/10* (2013.01); *A01N 59/02* (2013.01); *A01N 59/16* (2013.01); *A61K 9/146* (2013.01); *C01B 19/002* (2013.01); *C01B 19/007* (2013.01)

(58) Field of Classification Search
CPC ...... A61K 33/24; A61K 9/146; C01B 19/002; C01B 19/007; A01N 59/02; A01N 59/16
See application file for complete search history.

(56) References Cited

PUBLICATIONS

Badawi et al., "Surface and Biological Activity of Organoammonium Hydrogen Selenite Surfactants", J Surfact Deterg, 10, 2007, pp. 257-267.*
Badawi et al, "Surface and Biological Activity of Organoammonium Hydrogen Selenite Surfactants", J. Surfact. Deterg., 2007, 10: 257-267. (Year: 2007).*
Gupta et al, "Combination of sulfamethazole and selenium in anticancer therapy: a novel approach", Dec. 2013, vol. 384, Issue 1-2, pp. 279-285. (Year: 2013).*
Badawi et al, "Copper (II)-Surfactant Complex and its Nano Analog as Potential Antitumor Agents", 30:1303-1309, 2009. (Year: 2009).*
Kelland, "The resurgence of platinum-based cancer chemotherapy", Nature Reviews, vol. 7, Aug. 2007, pp. 573-584. (Year: 2007).*

* cited by examiner

*Primary Examiner* — Rachael E Bredefeld
(74) *Attorney, Agent, or Firm* — Geeta Kadambi Riddhi IP LLC

(57) ABSTRACT

The present application discloses a method of synthesizing metal-based cationic surfactants and further their usage as anti-tumor and anti-bacterial agents. For the synthesis, selenius acid is mixed with sulfonamide to form sulfonammonium hydrogen selenites. Cobalt and Platinum hydrogen selenite dehydrate were then synthesized, and refluxed with sulfonammonium hydrogen selenites to form the disclosed Cobalt/Platinum ammonium hydrogen selenite complexes. Both complexes were mixed with cyclodextrin oligosaccharide to form nanoparticles, which were tested for anti-tumor/cancer and anti-bacterial effects.

4 Claims, No Drawings

METHOD OF MAKING METAL BASED CATIONIC SURFACTANT NANO PARTICLES AND THEIR USE

CROSS REFERENCE TO RELATED APPLICATION

The instant application s a national stage entry application and claims priority to now pending PCT application PCT/IB2014/001752 filed on Apr. 1, 2014. The pending and now allowed U.S. Utility Application PCT/IB2014/001752 is hereby incorporated by reference in its entireties for all of its teachings.

FIELD OF TECHNOLOGY

The disclosure relates generally to a method of synthesizing and using a complex nano particle to be used as a biocide. More specifically, the disclosure relates to a method of synthesizing Cobalt and/or Platinum ammonium hydrogen selenite as nano-particles and using as anti-tumor and/or anti-bacterial agent.

BACKGROUND

Selenium ranks 70th in abundance among the known elements and constitutes approximately $10^{-5}$% of the Earth's crust (Edmonds et. al, 2000), Selenium compounds are known to act as anticancer agent, both in intact animals and in cellular systems (Medina et. al. 1988, Verne et al. 1984). The chemo preventive action of selenium compounds have been suggested to result from inhibitory effects on carcinogen activation and the potentiation of the immune system. In addition, a compound such as selenite has been shown to reduce toxicity and enhance anti-tumor activities of different drugs (Menter et. al. 2000, Zeng et. al. 2002). The cationic surfactants and their metal complexes showed good biological activity towards different types of microorganisms owing to their higher ability towards adsorption at the cell membranes. However, there are many technical difficulties in synthesizing the metal complexes showing excellent biological activity.

There is a need for synthesizing nanoparticles composed of different chemical compositions which may be used as different anti-neoplastic drugs.

SUMMARY

The instant invention discloses a method of making and using a complex nano-particle as a biological agent. Further, the invention discloses a method of making and using a complex nano-particle as an anti-tumor agent. Also, the invention discloses a method of making and using a complex nano particle as an anti-bacterial agent.

In one embodiment, the present invention discloses a method of making and using a cationic surfactant nano-particle as a biological agent. In another embodiment, the present invention discloses a method of making and using a cationic surfactant nano-particle as an anti-tumor agent. In most embodiments, the present invention discloses a method of making and using a cationic surfactant nano-particle as an anti-bacterial agent.

In one embodiment, the present invention discloses a method of making and using a cationic surfactant nano-particle as Platinum (Pt) or a Cobalt (Co) complex.

Thus, one embodiment of the invention discloses a method of making and using a Co/Pt cationic surfactant complex as an anti-tumor agent. In another embodiment, the present invention discloses a method of making and using a Co/Pt cationic surfactant complex as an anti-bacterial agent.

Further, in one embodiment, synthesis of a hydrogen selenite is disclosed. In another embodiment, synthesis of a sulfonammonium hydrogen selenite is disclosed. The synthesis as disclosed comprises: mixing stoichiometric amounts of a selenius acid and a sulfonamide in an ethyl alcohol and making a solution; stirring the solution till the precipitation is stopped; filtering a precipitate formed; washing the precipitate by ethyl alcohol and crystallizing the precipitate by diethyl ether.

In one embodiment, a process to synthesize a metal complex is disclosed for a transition metal complex such as Pt and a carbon metal complex such as Co.

In one embodiment, synthesis of a Pt metal complex as a Pt hydrogen selenite dehydrate is disclosed comprising: reacting a selenius acid with a Pt carbonate as $Pt(OH_2)_2CO_3$ to form a precipitate; washing the precipitate till the absence of a foreign ion followed by filtration; leaving the filtrate at room temperature for crystallization; washing the crystals; drying the crystals in air and forming a Pt metal complex as a Pt hydrogen selenite dehydrate complex as shown in equation 1:

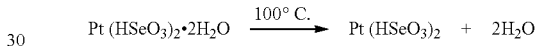

(Equation 1)

$$Pt(HSeO_3)_2 \cdot 2H_2O \xrightarrow{100°C.} Pt(HSeO_3)_2 + 2H_2O$$

In another embodiment, synthesis of a Co metal complex as a Co hydrogen selenite dehydrate is disclosed comprising: reacting a selenius acid with a Co carbonate as a $Co(OH_2)_2(CO_3)_2$ to form a precipitate; washing the precipitate till the absence of a foreign ion followed by filtration; leaving the filtrate at room temperature for crystallization; washing the crystals; drying the crystals in air and forming a Co metal complex as a Co hydrogen selenite dehydrate complex as shown in equation 2:

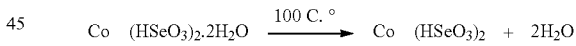

(Equation 2)

$$Co(HSeO_3)_2 \cdot 2H_2O \xrightarrow{100\,C.°} Co(HSeO_3)_2 + 2H_2O$$

The crystals formed in the above mentioned process may be washed with water or other non-aqueous solution.

In one embodiment, selenius acid and metal carbonate such as Pt and Co carbonate is mixed in equimolar amounts whereas in another embodiment selenius acid and metal carbonates such as Pt and Co carbonate may be mixed in the ratio of 1:2, 1:3, 2:1, 3:1 and other ratio's depending on the experimental setup. In one embodiment, selenius acid and metal carbonate such as $Pt(OH_2)_2 CO_3$ or as $Co(OH_2)_2 (CO_3)_2$ are mixed in water whereas in other embodiment selenius acid and metal carbonate such as $Pt(OH_2)_2 CO_3$ or as $CO(OH_2)_2 (CO_3)_2$ are mixed in a desired medium.

Further, filtrate for forming a metal complex such as a Pt or a Co complex may be kept at 37° C. for 24 hours or at a desired temperature for a pre-set interval of time.

In one embodiment, a process to synthesize a metal selenite surfactant is disclosed. In another embodiment, a process to synthesize a Pt selenite complex as a Pt ammonium hydrogen selenite complex is disclosed. In various other embodiments, a process to synthesize a Co selenite complex as a Co ammonium hydrogen selenite complex is disclosed. The process as disclosed comprise of: refluxing a sulfonammonium hydrogen selenite with a Pt hydrogen selenite or a Co hydrogen selenite in ethyl alcohol to form a product; purifying the product formed and forming a crystal; recrystallizing the product in petroleum ether and washing the recrystallized crystal with diethyl ether to form a Pt/Co ammonium hydrogen selenite complex with a general formula $[RN^+H_3]_2 [Pt(HSeO_3)_4]^{-2}$ or $[RN^+H_3]_2 [Co(HSeO_3)_6]^{-2}$ respectively.

The process as disclosed, further comprise of mixing 2 moles of sulfonammonium hydrogen selenite with one mole of metal hydrogen selenite such as Pt/Co selenite.

Further, the invention also discloses a process to reduce a metal complex as formed above such as Pt/Co complex into a nano sized particle to produce a cationic surfactant nano-particle. The process, comprise of mixing the metal complexes such as the Pt/Co complexes as formed above mechanically with a cyclodextrin oligosaccharide and grinding to a nano-sized particles resulting in the production of a cyclodextrin metal complex nano-particle.

The presently disclosed complexes (Pt and Co complexes) act as cationic surfactants. Further, characterization of cationic surfactants such as Pt/Co surfactant is performed to prove superior functional qualities of the synthesized nano-particles.

In one embodiment, anti-tumor activity of a metal cationic surfactant is disclosed wherein cancer cell lines of various concentration and types were treated with disclosed cationic surfactants and its anti-tumor activity was assessed.

In another embodiment, anti-bacterial activity of a metal cationic surfactant is disclosed wherein bacterial contamination such as sulphur reducing bacterial contamination has been reduced by reducing cell viability.

Other features may be apparent from the accompanying detailed description that follows.

DETAILED DESCRIPTION

The invention discloses a method to synthesize cationic surfactants nano-particles comprising of cyclodextrin and Pt/Co complex. Further, the invention also discloses a method of using the synthesized cationic surfactant nano-particle comprising of cyclodextrin and Pt/Co complex as anti-tumor and/or anti-bacterial agents.

Synthesis of Sulfonammonium Hydrogen Selenites

All chemicals were produced from sigma Aldrich company such as selenius acid; sulfonamide; ethyl alcohol; diethyl ether; $PtCl_2$; $CoCl_4$; sulfonammonium hydrogen selenites; Cobalt or platinum hydrogen selenite; petroleum ether; cyclodextrin oligosaccharide.

To carry out the synthesis process, stoichiometric amounts of selenius acid were mixed with sulfonamide at room temperature in ethyl alcohol and then stirred until the precipitation is formed. The precipitant was then filtered and washed by ethyl alcohol to form crystals. The crystals were then recrystallized using diethyl ether as disclosed as previously known (Pavel et. al. 2003). The products thus formed is designated as $II_a$ and have the general formula: $RN^+H_3$ $HSeO_3$ ($II_a$) where R=sulfon Synthesis of Metal Complexes:

For obtaining Pt and/or Co hydrogen selenite dehydrate; selenius acid ($H_2SeO_3$) is reacted with basic $Co(OH_2)_2(CO_3)_2$ and $Pt(OH_2)_2 CO_3$ to form a precipitate (Equation 3) which has been prepared by mixing aqueous solutions of equimolar amounts of $PtCl_2$ and but for $CoCl_4$ the ratio is 1:2. The precipitate is then washed till one see the absence of foreign ions.

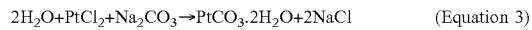

$2H_2O+PtCl_2+Na_2CO_3 \rightarrow PtCO_3.2H_2O+2NaCl$ (Equation 3)

To carry out the above disclosed synthesis: An aqueous solution of 2 g (0.016 mol) $H_2SeO_3$ in 10 ml water, was added to a warm solution of the freshly prepared Co carbonate 0.512 g (0.008 mol) in 10 ml water. The obtained solution is then filtered and kept at room temperature for crystallization for 2 days following which crystalline prisms are formed. The crystals produced are filtered and washed with water followed by drying in air (Gulya et. al. 1992). For obtaining Pt (II) hydrogen selenite dihydrate an aqueous solution of 2 g $H_2SeO_3$ in 10 ml water was added to a warm solution of the freshly prepared Pt carbonate 1.28 g in 10 ml water. The obtained solution is filtered and kept at room temperature for crystallization for 24 hour following which blue color crystalline prisms are formed.

(Equation 4)

$$Pt\ (HSeO_3)_2.2H_2O \xrightarrow{100\ C.°} Pt\ (HSeO_3)_2 + 2H_2O$$

Synthesis of Pt and/or Co Ammonium Hydrogen Selenite Complex

Co or Pt sulfonammonium hydrogen selenite complexes were prepared (as shown via equations 6 and 7) by refluxing two moles of sulfonammonium hydrogen selenites ($II_a$) with one mole of Co or Pt hydrogen selenite in ethyl alcohol for two hours approximately or for a desired time period. The products were designated as ($II_{b\ and\ c}$) respectively. The reaction is carried out between 100° C.-110° C. (Equation 5).

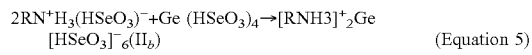

$2RN^+H_3(HSeO_3)^- + Ge\ (HSeO_3)_4 \rightarrow [RNH3]^+_2 Ge\ [HSeO_3]^-_6 (II_b)$ (Equation 5)

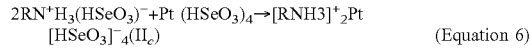

$2RN^+H_3(HSeO_3)^- + Pt\ (HSeO_3)_4 \rightarrow [RNH3]^+_2 Pt\ [HSeO_3]^-_4 (II_c)$ (Equation 6)

The products as shown with formula in equation 5 and 6($II_b$, $II_c$) respectively were purified and recrystallized three times in petroleum ether and then washed with diethyl ether. The products kept in desiccators till it's use.

Preparation of Pt and/or Co Ammonium Hydrogen Selenite Complex Nano-Particles

The Co and Pt selenite complexes (as from herein onwards cationic surfactants) were mixed mechanically with the cyclodextrin oligosaccharide using vortex followed by grinding to the nano sized particles using ball mill model PM 400 at 200 rpm for 10 hrs. The cationic surfactant nano-particles loaded cyclodextrin nanoparticles were obtained and their particle size was determined using transmission electron microscope (TEM). Further, the particle size distribution of the product was measured using laser particle size analyzer (FRITSCH) model Analystte 22.

Surface Properties of the Synthesized Cationic Surfactants

As shown in Table 1, complexing ammonium hydrogen selenite with Co or Pt ions, a high depression in CMC value was observed for compounds designated as $II_b$ and ($II_c$ as compared with those of the complex designated as $II_a$.

This could be explained from the unique property of the metal complexes in water. The complexes retain their unity in the solutions, which increased their volume in the aqueous media resulting in repulsion between the hydrophobic chain of the complexes and water molecules. ($II_{ac}$). Platinum surfactant has been found to be the most efficient one in because it achieved the maximum reduction of the surface tension at CMC. Further, the efficiency "$P_{C20}$" increase with increasing molar ratio of methylene units. These are due to the fact that the efficiency of adsorption at interfaces increase linearly with increase in the carbon atoms in hydrophobic group (Rosen et. al. 1987). In case of the prepared $II_a$ surfactants by increasing the number of methylene units maximum surface excess $\Gamma_{max}$ increases. Complexing the cationic surfactant with Co and/or Pt ions contributes to migration of molecules to the water-air interface causing a consequent increase in $\Gamma_{max}$ values. The consequence increase of $\Gamma_{max}$ leads to crowdedness occurring at the interface which causes a decrease in the minimum area per molecule $A_{min}$ values. That is due to the minimum surface area decrease with increasing the hydrophobic chain length of the synthesized surfactant molecules. Further, the standard free energies of micellization $\Delta G^0{}_{mic}$ and adsorption $\Delta G^0{}_{ads}$ values are always negative indicating the spontaneously of these two processes but there is more increase in negativity of $\Delta G^0{}_{ads}$ rather than those of micellization indicating the tendency of the molecules to be adsorbed at the interface.

TABLE 1

Physical characterization of synthesized surfactants using different parameters:

| Comp. No. | CMC × $10^{-3}$ | $\gamma_{CMC}$ (mN/m) | $\Pi_{CMC}$ (mN/m) | $P_{C20}$ (Mole/L) | $\Gamma_{max} \times 10^{-11}$ (Mole/cm$^2$) | $A_{min}$ (nm$^2$) | $\Delta G_{ads}$ | $\Delta G_{mic}$ | $\Delta G_{ads}/A_{min}$ |
|---|---|---|---|---|---|---|---|---|---|
| $II_a$ | 1.2 | 32 | 40 | 3.9 | 10.4 | 1.5 | −67.7 | −34.1 | −46.8 |
| $II_b$ | 1.1 | 30 | 42 | 4.1 | 10.2 | 1.5 | −69.9 | −34.8 | −49.1 |
| $II_c$ | 0.80 | 29 | 43 | 4.3 | 11.1 | 1.45 | −71.1 | −35.3 | −50.2 |

Anti-Tumor Properties of Cationic Surfactants

Olylammonium hydrogen selenite's with its Co and/or Pt complexes were investigated as potential and selective anticancer pro-drugs. They were tested by using Ehrlich Acites Carcinoma (EAC) as a model system of mice cell tumor. A line of Ehrlich ascites carcinoma (EAC) as used in the present study had been kindly supplied from National Cancer Institute, Cairo, Egypt, and maintained in female Swiss albino mice through weekly IMP transplantation of $2.5 \times 10^6$ tumor cells/mouse. EAC cells were obtained by needle aspiration under aseptic condition. The aseptic fluid was diluted with sterile saline so that 0.1 ml contains $2.5 \times 10^6$ cells counted microscopically using a haemocytometer. The disclosed compounds were also tested in vitro on human five monolayer tumor cell lines such as $MCF_7$ (Breast carcinoma), $HEPG_2$ (liver carcinoma), $U_{251}$ (Hela tumor) and $HCT_{116}$ (colon carcinoma).

EAC cells as a model system was based on the finding that it is excellent tool for studying the biological behavior of malignant tumors and drug action with cells (Hamburger A. W. 1981). In vitro studies of the disclosed cationic surfactants anti-tumor activity was determined according to the percentage of nonviable cells (NVC %) which was calculated by the following equation:

NVC %=[number of NVC/total number of cells]100    (Equation 10)

Micelles are known to prevent the mobility and suppress anti-tumor activity. Sulfonammonium hydrogen selenite does not reach to $L_{50}$ for all tested human monolayer tumor cell lines. Many targets may be explored to counteract cancer and indication the role of studied metals should be useful for a better use of metal-based anticancer drugs.

Anti-Bacterial Properties of Presently Disclosed Cationic Surfactants

Sulphur reducing bacteria (SRB) are strict anaerobes that are often found in biotopes where toxic conditions can temporarily exist. The bacteria have developed several defense strategies in order to survive under exposure to oxygen. These strategies include peculiar behaviors in the presence of oxygen, like aggregation or aerotaxis, and enzymatic systems dedicated to the reduction and the elimination of oxygen and its reactive species. SRB are mainly sulfate reducers and their growth frequently causes severe corrosion problems in oil well pipes. Due to the economic losses as well as environmental health and safety hazards caused by the activity of stabilized mixed culture containing SRB, SRB in many industrial sectors such as the oil and gas industry, it is important to minimize the risks resulting from SRB activity.

Ammonium compounds are known to be most effective against anaerobic bacteria (e.g. those that occur in oil wells). Several studies indicate that some quaternary ammonium compounds act as corrosion inhibitors and decrease sulfide production by SRB at low concentration than some biocides of commercial source. The results of the disclosed cationic surfactants against sulphur reducing bacteria are recorded in Table 2.

TABLE 2

Inhibition zone diameter (mm/mg sample) for the disclosed cationic surfactants against sulphur reducing bacteria.

| Sample | Inhibition zone diameter (mm/mg sample) Sulphur reducing bacteria |
|---|---|
| $II_a$ | 22 |
| $II_b$ | 20 |
| $II_c$ | 18 |

The results in Table 2 indicate that the new synthesized cationic surfactants have high antimicrobial activity against sulphur reducing bacteria, and the difference in activity depends on the length of hydrophobic chain. The optimal length of the alkyl chain has been noted to be ten carbon atoms. The highest results were achieved by platinum complexes, this may be due to platinum is oxidizing agent act as reduction inhibitors leading to decrease in sulfide production and decreasing the growth rate of anaerobic (SRB). In more general bacterial growth Inhibition by metal ions was investigated in the sulphate-free medium. The rate of $H_2S$ production was approximately directly proportional to the specific activities of the invested enzymes. These activities were inversely proportional to the generation time. The rate of microbiologically induced corrosion (MIC) of carbon steel was directly proportional to bacterial resistance to metal ions.

While the present disclosure has been described with reference to an exemplary embodiment, changes may be made within the purview of the appended claims, without departing from the scope and spirit of the present disclosure in its aspects. Also, although the present disclosure has been described herein with reference to particular materials and embodiments, the present disclosure is not intended to be limited to the particulars disclosed herein; rather, the present disclosure extends to all functionally equivalent structures, methods and uses, such as are within the scope of the instant claims. Accordingly, the specification and drawings are to be regarded in an illustrative rather than in a restrictive sense.

What is claimed is:

1. A process, comprising:
   refluxing a sulfonammonium hydrogen selenite with a metal hydrogen selenite dehydrate in ethyl alcohol to form a product;
   purifying the product to form a filtrate;
   forming a crystal using the filtrate;
   recrystallizing the crystal in petroleum ether and washing a recrystallized crystal with a diethyl ether to form a metal ammonium hydrogen selenite complex; and
   mixing the metal ammonium hydrogen selenite complex with a cyclodextrin oligosaccharide to form a nanoparticle as a metal based cationic surfactant, wherein the metal is platinum.

2. The process of claim 1, wherein the nanoparticle as the metal based cationic surfactant acts as an anti-tumor agent.

3. The process of claim 1, wherein sulfonammonium hydrogen selenite formed has a general formula $RN^+H_3 HSeO_3$, wherein R represents a sulfone.

4. The process of claim 1, wherein the filtrate is left for 24 hours to form the crystal.

* * * * *